United States Patent [19]

Sudilovsky

[11] Patent Number: 5,049,553

[45] Date of Patent: Sep. 17, 1991

[54] METHOD FOR PREVENTING OR TREATING SYMPTOMS RESULTING FROM CLOSED HEAD INJURIES EMPLOYING AN ACE INHIBITOR

[75] Inventor: Abraham Sudilovsky, Lawrenceville, N.J.

[73] Assignee: E. R. Squibb & Sons, Inc., Princeton, N.J.

[21] Appl. No.: 460,704

[22] Filed: Jan. 4, 1990

[51] Int. Cl.$^5$ .................... A61K 31/675; A61K 31/40
[52] U.S. Cl. ...................................... 514/91; 514/422; 514/423
[58] Field of Search .......................... 514/423, 91, 422

[56] References Cited

U.S. PATENT DOCUMENTS 4,906,614 3/1990 Giertz et al. ........................... 514/18

OTHER PUBLICATIONS

Deicken, Biol. Psychiatry, 1986, 21:1425-28.
Germain et al., Biol. Psychiatry, 1988, 23:637-641.
Zubenko, Am. J. Psychiatry, 141:110-111 (1984).
Medical Tribune, vol. 29, No. 28, Thurs., Oct. 13, 1988.
Therapy Review, Drug Therapy of Hypertensive Crises, J. L. Stumpf, Clinical Pharmacy, vol. 7, Aug. 1988, pp. 582-591.
Sudilovsky et al, "Captopril Delays Extinction of Conditioned Avoidance Response in the Rat," Poster Presentation, 14th Congress of the Collegium Internationale Neuro-Psychopharmacologicum, Florence, Jun. 1984 (Abstracts, CINP, 1984, 397).

Primary Examiner—Frederick E. Waddell
Assistant Examiner—Raymond J. Henley, III
Attorney, Agent, or Firm—Burton Rodney

[57] ABSTRACT

A method is provided for preventing onset of or treating symptoms resulting from closed head injuries, in hypertensive or normotensive patients, by administering an ACE inhibitor, for example captopril, zofenopril, fosinopril, ceranapril, enalapril or lisinopril.

15 Claims, No Drawings

METHOD FOR PREVENTING OR TREATING SYMPTOMS RESULTING FROM CLOSED HEAD INJURIES EMPLOYING AN ACE INHIBITOR

FIELD OF THE INVENTION

The present invention relates to a method for preventing or treating symptoms resulting from a closed head injury in mammalian species by administering an ACE inhibitor, such as captopril, ceranapril, fosinopril, enalapril or lisinopril.

BACKGROUND OF THE INVENTION

Victims of closed head injuries caused by a traumatic event, such as a blow to the head, may suffer a loss of consciousness and will likely sustain a concussion. In such event, even though the victim may recover consciousness, without apparent permanent injury, still, he may suffer from an array of symptoms brought on by the traumatic injury, especially if he has been unconscious for 20 minutes or more before revival. Examples of such symptoms brought on by trauma which causes unconsciousness for 20 minutes or more include memory loss, poor balance, headache, disorientation, dissociation of thought, rages, black out, garbled speech and depression.

Medical Tribune, Vol. 29, No. 28, Thurs., Oct. 13, 1988, reports that "clinical and anecdotal evidence is mounting that the opiate antagonist naltrexone (Trexan, DuPont), a longacting oral congener of naloxone (Narcan, DuPont), may be 'meritorious' in relieving numerous symptoms of postconcussion syndrome . . . "

Therapy Review, Drug therapy of hypertensive crises. J.L. Stumpf, Clinical Pharmacy, Vol. 7, Aug. 1988, pp 582-591, discloses in the Abstract that "factors that may precipitate a hypertensive crisis include . . . head injuries . . . " and that "captopril . . . have been used with some success."

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-phenylbutyl)phosphinyl]-oxy]-1-oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

It has now been found that angiotensin converting enzyme inhibitors, especially mercapto containing ACE inhibitors such as captopril and zofenopril, are capable of reducing and, in some cases, preventing symptoms resulting from closed head injuries.

DESCRIPTION OF THE INVENTION

In accordance with the present invention, a method is provided for preventing onset of or treating symptoms resulting from closed head injury in a mammalian species, wherein a therapeutically effective amount of angiotensin converting enzyme inhibitor is administered systemically, such as orally or parenterally.

The term "closed head injury" as employed herein refers to a traumatic injury to the head which is the result of a blow to the head which causes loss of consciousness for a period of at least 20 minutes, and which usually causes a concussion.

Examples of symptoms resulting from closed head injuries, brought on by trauma which causes unconsciousness for 20 minutes or more, and which may be treated by an ACE inhibitor in accordance with the method of the invention include memory loss, poor balance, headache, disorientation, dissociation of thought, rages, black out, garbled speech and depression.

The ACE inhibitor may be administered to hypertensive patients or normotensive patients in accordance with the method of the present invention.

In preferred embodiments where the patient to be treated in accordance with the present invention is normotensive, the angiotensin converting enzyme inhibitor may be administered in amounts below that required to cause hemodynamic effects, that is below that required to cause a reduction in blood pressure. Where the patient to be treated is hypertensive, then the angiotensin converting enzyme inhibitor may be employed in amounts usually employed to treat hypertension.

The angiotensin converting enzyme inhibitor which may be employed herein preferably includes those containing a mercapto (-S-) moiety such as substituted proline derivatives, such as any of those disclosed in U. S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U. S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

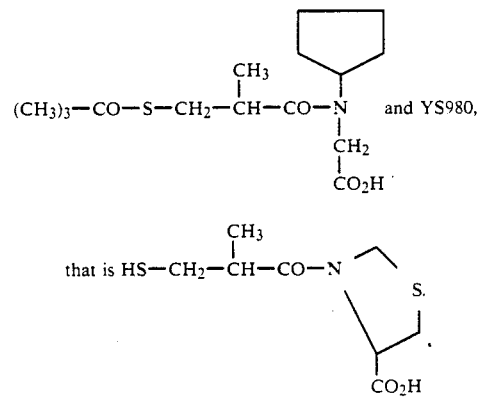

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U. S. Pat. No. 4,452,790 with (S)-1-[6- amino-2-[[hydroxy-(4-phenylbutyl)-phosphinyl]oxy]-1-oxohexyl]-L-proline (SQ 29,852 or ceranapril) being preferred. phosphinylalkanoyl prolines disclosed in U.S. Pat. No. 4,168,267 mentioned above with fosinopril being preferred, any of the phosphinylalkanoyl substituted prolines disclosed in U. S. Pat. No. 4,337,201, and the phosphonamidates disclosed in U. S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U. S. Patent No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U. S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U. S. Pat. No. 4,344,949 and CI 925 (Warner-Lambert) ([3S-[2[R(*)R(*)]]3R(*)]-2-[2-[[1-(ethoxycarbonyl )-3-phenylpropyl]amino[-1-oxopropyl]-1,2,3,4,-tetrahydro-6,7-dimethoxy-3-isoquinoline-carboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives such as captopril, zofenopril, fosinopril, ceranapril, enalapril or lisinopril.

The above-mentioned U.S. patents are incorporated herein by reference.

In carrying out the method of the present invention, the angiotensin converting enzyme inhibitor may be administered to mammalian species, such as horses, cattle, dogs, cats, and humans, and as such may be incorporated in a conventional systemic dosage form, such as a tablet, capsule, elixir or injectable, as well as suppository dosage forms that release ACE inhibitor in the bloodstream. The above dosage forms will also include the necessary carrier material, excipient, lubricant, buffer, bulking agent (such as mannitol), antioxidants (ascorbic acid of sodium bisulfite) or the like. Oral dosage forms are preferred, although parenteral forms such as intramuscular, intraperitoneal, or intravenous enema and suppository forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg.

A preferred oral dosage form, such as tablets or capsules, will contain the ACE inhibitor in an amount of from about 0.1 to about 500 mg, preferably from about 2 to about 200 mg, and more preferably from about 3 to about 150 mg.

For parenteral administration, the ACE inhibitor will be employed in an amount within the range of from about 0.005 mg/kg to about 10 mg/kg and preferably from about 0.01 mg/kg to about 1 mg/kg.

The composition described above may be administered in the dosage forms as described above in single or divided doses of one to four times daily. It may be advisable to start a patient on a low dose and work up gradually to a high dose.

Tablets of various sizes can be prepared, e.g., of about 5 to 700 mg in total weight, containing the active substance in the range described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending the active substance in a conventional liquid vehicle acceptable for pharmaceutical administration so as to provide the desired dosage in one to four teaspoonfuls.

Such dosage forms can be administered to the patient on a regimen of one to four doses per day.

Suppository formulations containing from about 5 to about 250 mg ACE inhibitor may be prepared as well using a conventional suppository base (such as disclosed in U.S. Pat. Nos. 4,344,968, 4,265,875, and 4,542,020) so as provide the desired dosage in one to four suppositories per day.

As indicated, where the patient to be treated is normotensive, then smaller amount of angiotensin converting enzyme inhibitor may be employed, that is below that required to reduce blood pressure. For example, for oral dosage forms, normotensives may be treated with from about 0.01 mg/kg to about 1 mg/kg or from about 1 mg to about 6 mg, one to four times daily.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

The formulations as described above will be administered for a prolonged period, that is, for as long as it is necessary to prevent or treat symptoms resulting from closed head injuries. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

A captopril formulation suitable for oral administration in preventing onset of or treating symptoms resulting from closed head injuries in hypertensive or normotensive patients is set out below.

1000 tablets each containing 100 mg of 1-[(2S)-3-mercapto-2-methylpropionyl]-L-proline were produced from the following ingredients.

| | |
|---|---|
| 1-[(2S)-3-Mercapto-2-methylpropionyl]-L-proline (captopril) | 100 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for preventing onset of or treating symptoms resulting from closed head injuries as described above.

EXAMPLE 2

1000 tablets each containing 200 mg of captopril are produced from the following ingredients:

| | |
|---|---|
| Captopril | 200 g |
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in preventing onset of or treating symptoms resulting from closed head injuries in normotensive or hypertensive patients.

EXAMPLE 3

Two piece #1 gelatin capsules each containing 5 mg of captopril are filled with a mixture of the following ingredients:

| | |
|---|---|
| Captopril | 5 mg |
| Magnesium stearate | 7 mg |
| USP lactose | 193 mg. |

The resulting capsules are useful in preventing onset of or treating symptoms resulting from closed head injuries in normotensive or hypertensive patients.

EXAMPLE 4

An injectable solution for use in preventing onset of or treating symptoms resulting from closed head injuries in normotensive or hypertensive patients.

| | |
|---|---|
| Captopril | 500 mg |
| Methyl paraben | 5 mg |
| Propyl paraben | 1 mg |
| Sodium chloride | 25 g |
| Water for injection qs. | 5 l. |

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 5 to 8

Dosage forms for use in preventing onset of or treating symptoms resulting from closed head injuries in normotensive or hypertensive patients, in such patients are prepared as described in Examples 1 to 4 except that N-(1-ethoxycarbonyl-3-phenylpropyl)-L-alanyl-L-proline (enalapril) is used in place of captopril.

EXAMPLE 9 and 10

A suppository formulation containing conventional suppository base such as any of those disclosed in U.S. Pat. Nos. 4,344,968, 4,265,875 or 4,542,020, and N-(1-ethoxy-carbonyl-3-phenyl- propyl)-L-alanyl-L-proline (40 mg), (enalapril) or captopril (25 mg), is prepared and is used to prevent onset of or treating symptoms resulting from closed head injuries in normotensive or hypertensive patients.

EXAMPLE 11

A zofenopril formulation suitable for oral administration in preventing onset of or treating symptoms resulting from closed head injuries in normotensive or hypertensive patients is set out below.

1000 tablets each containing 100 mg of zofenopril are produced from the following ingredients.

| | |
|---|---|
| [1(S),4(S)]-1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating closed head injury as described above.

EXAMPLE 12

A modified release beadlet formulation capable of slowly releasing the angiotensin converting enzyme inhibitor captopril over a period of up to 6 hours and having the following composition was prepared as described below.

| Ingredient | Amount in Parts by Weight |
|---|---|
| Captopril | 27 |
| Citric aicd | 30 |
| Microcrystalline cellulose* | 43 |

*amount may vary to reflect chemical purity of captopril

The above ingredients were mixed and kneaded using water in a planetary mixer to form a wet mass. The wet mass was passed through a Nica E140 extruder to form an extrudate (~1 mm diameter). The extrudate was then passed through a Nica spheronizer to form beadlets. The beadlets were then dried at 40° C. for 12-18 hours in a tray drying oven or for 2-4 hours in a fluid bed dryer. A fraction of the so-formed beadlets were filled into hard shell pharmaceutical capsules for use in preventing onset of or treating symptoms resulting from closed head injuries in hypertensive or normotensive patients.

EXAMPLE 13

A modified release coated-beadlet formulation having the following composition was prepared as follows.

|  |  |  | mg/dose |
|---|---|---|---|
| (i) | Core | | |
| | Captopril | | 5 mg |
| | Microcristalline cellulose | | 159.1 mg |
| | Citric acid | | 37 mg |
| | Lactose | | 74.1 mg |
| (ii) | Sealcoat | | |
| | Hydroxypropyl methyl cellulose | ca. | 8.3 mg |
| | Polyethylene glycol | ca. | 2.8 mg |
| (iii) | Barriercoat | | |
| | Cellulose acetate phthalate | ca. | 4.2 mg |
| | Acetylated monoglycerides (Myvacet ®9-40) | ca. | 1.3 mg |

The beadlet cores were prepared as described in Example 12. After the dried beadlets were formed, they were coated via a two step process as follows. An aqueous solution of hydroxypropyl methyl cellulose (7.5% by weight) and polyethylene glycol (2.5% by weight) was prepared and sprayed on to the beadlets to form a sealcoat. The beadlets were then coated with a barriercoat using an aqueous dispersion of cellulose acetate phthalate (30% by weight) mixed with acetylated monoglycerides (9.5% by weight). The beadlets were then filled into hard shell pharmaceutical capsules which are useful in preventing onset of or treating symptoms resulting from closed head injuries in normotensive patients.

EXAMPLE 14

A modified release coated-beadlet formulation having the following composition was prepared as follows.

| Ingredient | | % by Weight of Coated Beadlet |
|---|---|---|
| Core | | |
| Captopril | | 26.2 |
| Citric acid | | 29.1 |
| Microcrystalline cellulose | | 41.8 |
| Film coating | | |
| Hydroxypropylmethyl cellulose phthalate | ca. | 2.6 |
| triethyl citrate | ca. | 0.3 |

The beadlet cores were prepared as described in Example 12.

Hydroxypropylmethyl cellulose phthalate (9 parts) and triethylcitrate (1 part) were dissolved in ethyl alcohol (90 parts) and then sprayed on to the beadlets to form coated product. The so-formed beadlets were then filled into hard shell pharmaceutical capsules which are useful in preventing onset of or treating symptoms resulting from closed head injuries in hypertensive or normotensive patients.

EXAMPLES 15 to 19

Following the procedure of Examples 13 to 15 except substituting the following ACE inhibitor, organic acid and binder-excipients, the following beadlet compositions may be prepared which are useful in preventing onset of or treating symptoms resulting from closed head injuries in hypertensive or normotensive patients.

| Ex. No. | ACE Inhibitor | Organic acid | Binder |
|---|---|---|---|
| 15. | N-(1-ethoxycarbonyl-3-phenylpropyl)-L-proline | Citric acid | Microcrystalline cellulose |
| 16. | (S)-1-[6-Amino-2-[[hydroxy(4-phenylbutyl)phosphinyl]oxy]-1-oxohexyl]-L-proline | Malic acid | Microcrystalline cellulose and hydroxypropyl methyl cellulose |
| 17. | Lisinopril | Tartaric acid | Na carboxymethyl cellulose |
| 18. | Zofenopril | Succinic acid | Gelatin, pectin and Na carboxymethyl cellulose |
| 19. | Fosinopril | Maleic acid | Microcrystalline cellulose |

EXAMPLE 20

By substituting 5 g of pivopril for the zofenopril in Example 11, 1000 tablets each containing 5 mg of the pivopril are produced which is useful in preventing onset of or treating symptoms resulting from closed head injuries in normotensive patients.

EXAMPLE 21

1000 tablets each containing 200 mg of YS890 are produced from the following ingredients:

| | |
|---|---|
| YS890 | 200 g |
| Lactose | 100 g |
| Avicel | 150 g |
| Corn starch | 50 g |
| Magnesium stearate | 5 g |

The YS890, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in preventing onset of or treating symptoms resulting from closed head injuries in hypertensive or normotensive patients.

What is claimed is:

1. A method for preventing onset of or treating symptoms resulting from closed head injuries in a mammalian specie, which symptoms are poor balance, disorientation, dissociation of thought, rages, black out or garbled speech, which injuries are brought on by trauma which causes unconsciousness for 20 minutes or more, which comprises administering to a mammalian specie in need of such treatment an effective amount of an angiotensin converting enzyme inhibitor which is captopril, fosinopril, ceranapril, lisinopril, zofenopril, enalapril or fentiapril.

2. The method as defined in claim 1 wherein said mammalian specie is hypertensive.

3. The method as defined in claim 1 wherein said mammalian specie is normotensive.

4. The method as defined in claim 3 wherein the angiotensin converting enzyme inhibitor is administered below that amount required to effect a reduction in blood pressure.

5. The method as defined in claim 1 wherein said angiotensin converting enzyme inhibitor is administered orally or parenterally.

6. The method as defined in claim 1 wherein said angiotensin converting enzyme inhibitor is captopril.

7. The method as defined in claim 1 wherein said angiotensin converting enzyme inhibitor is zofenopril.

8. The method as defined in claim 1 wherein said angiotensin converting enzyme inhibitor is fentiapril.

9. The method as defined in claim 1 wherein said angiotensin converting enzyme inhibitor is captopril or zofenopril.

10. The method as defined in claim 1 wherein said angiotensin converting enzyme inhibitor is enalapril or lisinopril.

11. The method as defined in claim 1 wherein said angiotensin converting enzyme inhibitor is administered in single or divided doses of from about 0.1 to about 500 mg. one to four times daily.

12. The method as defined in claim 1 wherein said angiotensin converting enzyme inhibitor is administered in the form of tablets, capsules or by injection.

13. The method as defined in claim 1 wherein said angiotensin converting enzyme inhibitor is captopril or zofenopril and is administered systemically in an amount of from about 0.1 to about 500 mg. one to four times a day.

14. The method as defined in claim 1 wherein said angiotensin converting enzyme inhibitor is administered over a prolonged period of treatment.

15. A method for treating symptoms resulting from closed head injuries in a mammalian specie, which symptoms are poor balance, disorientation, dissociation of thought, rages, black out or garbled speech, which injuries are brought on by trauma which causes unconsciousness of 20 minutes or more, which comprises administering to a mammalian specie in need of such treatment an effective amount of an angiotensin converting enzyme inhibitor which is captopril, fosinopril, ceranapril, zofenopril, lisinopril, enalapril or fentiapril.

* * * * *